US010597562B2

(12) United States Patent
Briseno et al.

(10) Patent No.: US 10,597,562 B2
(45) Date of Patent: Mar. 24, 2020

(54) ELASTIC ATTACHMENT HOT MELT ADHESIVE COMPOSITION AND A DISPOSABLE ABSORBENT ARTICLE MADE WITH THE SAME

(71) Applicant: H.B. Fuller Company, St. Paul, MN (US)

(72) Inventors: Carlos Briseno, St. Paul, MN (US); Steven R. Vaughan, Lake Elmo, MN (US)

(73) Assignee: H.B. Fuller Company, St. Paul, MN (US)

( * ) Notice: Subject to any disclaimer, the term of this patent is extended or adjusted under 35 U.S.C. 154(b) by 134 days.

(21) Appl. No.: 15/668,412

(22) Filed: Aug. 3, 2017

(65) Prior Publication Data
US 2018/0037778 A1   Feb. 8, 2018

Related U.S. Application Data

(60) Provisional application No. 62/370,433, filed on Aug. 3, 2016.

(51) Int. Cl.
| | |
|---|---|
| *C09J 123/14* | (2006.01) |
| *B32B 7/12* | (2006.01) |
| *A61F 13/49* | (2006.01) |
| *C09J 123/12* | (2006.01) |
| *C09J 11/08* | (2006.01) |
| *B32B 5/18* | (2006.01) |
| *B32B 5/02* | (2006.01) |
| *B32B 5/22* | (2006.01) |
| *B32B 27/32* | (2006.01) |
| *B32B 29/00* | (2006.01) |
| *B32B 9/04* | (2006.01) |
| *B32B 21/04* | (2006.01) |
| *B32B 21/08* | (2006.01) |
| *B32B 23/08* | (2006.01) |
| *B32B 5/24* | (2006.01) |
| *B32B 27/22* | (2006.01) |
| *B32B 23/04* | (2006.01) |
| *B32B 27/12* | (2006.01) |
| *B32B 27/06* | (2006.01) |

(Continued)

(52) U.S. Cl.
CPC ....... *C09J 123/14* (2013.01); *A61F 13/49009* (2013.01); *A61L 15/585* (2013.01); *B32B 3/266* (2013.01); *B32B 5/022* (2013.01); *B32B 5/024* (2013.01); *B32B 5/18* (2013.01); *B32B 5/22* (2013.01); *B32B 5/245* (2013.01); *B32B 7/06* (2013.01); *B32B 7/12* (2013.01); *B32B 9/02* (2013.01); *B32B 9/045* (2013.01); *B32B 21/04* (2013.01); *B32B 21/047* (2013.01); *B32B 21/08* (2013.01); *B32B 23/04* (2013.01); *B32B 23/048* (2013.01); *B32B 23/08* (2013.01); *B32B 27/06* (2013.01); *B32B 27/065* (2013.01); *B32B 27/08* (2013.01); *B32B 27/10* (2013.01); *B32B 27/12* (2013.01); *B32B 27/22* (2013.01); *B32B 27/302* (2013.01); *B32B 27/32* (2013.01); *B32B 29/007* (2013.01); *C09J 11/08* (2013.01); *C09J 123/12* (2013.01); *A61F 2013/1591* (2013.01); *B32B 2262/02* (2013.01); *B32B 2262/0238* (2013.01); *B32B 2262/0246* (2013.01); *B32B 2262/0253* (2013.01); *B32B 2262/0276* (2013.01); *B32B 2262/0292* (2013.01); *B32B 2262/04* (2013.01); *B32B 2262/062* (2013.01); *B32B 2262/067* (2013.01); *B32B 2262/08* (2013.01); *B32B 2262/101* (2013.01); *B32B 2262/14* (2013.01); *B32B 2266/14* (2016.11); *B32B 2270/00* (2013.01); *B32B 2307/31* (2013.01); *B32B 2307/51* (2013.01); *B32B 2307/548* (2013.01); *B32B 2307/718* (2013.01); *B32B 2307/748* (2013.01); *B32B 2439/70* (2013.01); *B32B 2535/00* (2013.01); *B32B 2555/02* (2013.01); *B32B 2556/00* (2013.01); *C08L 2205/03* (2013.01)

(58) Field of Classification Search
CPC ........ C09J 123/14; C09J 123/12; C09J 11/08; A61F 13/49009; A61F 2013/1591; B32B 7/12; B32B 2555/02; B32B 2307/13; B32B 2307/718
See application file for complete search history.

(56) References Cited

U.S. PATENT DOCUMENTS

| | | |
|---|---|---|
| 4,037,601 A | 7/1977 | Denkinger |
| 4,046,945 A | 9/1977 | Baxman |

(Continued)

FOREIGN PATENT DOCUMENTS

| | | |
|---|---|---|
| EP | 1788058 | 5/2007 |
| WO | WO2009/100414 | 8/2009 |

(Continued)

*Primary Examiner* — Robert D Harlan
(74) *Attorney, Agent, or Firm* — Kirsten Stone; Kristi Halloran

(57) ABSTRACT

The invention features a hot melt adhesive composition based on olefin polymers that can be used for elastic attachment in the manufacture of a disposable article. The hot melt adhesive includes from about 3 to about 10% by weight of a first propylene-based copolymer having a melt index measured by ASTM D1238 (190° C., 2.16 kg) of no greater than about 5, a second propylene-based polymer with a viscosity at 190° C. of no greater than about 5000 cps, a first tackifying agent having a softening point of at least about 90° C. and from about 5% by weight to about 20% by weight of a plasticizer.

13 Claims, No Drawings

(51) Int. Cl.
  *B32B 9/02* (2006.01)
  *A61L 15/58* (2006.01)
  *B32B 7/06* (2019.01)
  *B32B 27/10* (2006.01)
  *B32B 27/08* (2006.01)
  *B32B 27/30* (2006.01)
  *B32B 3/26* (2006.01)
  *A61F 13/15* (2006.01)

(56) References Cited

U.S. PATENT DOCUMENTS

| | | |
|---|---|---|
| 4,075,382 A | 2/1978 | Chapman |
| 4,100,922 A | 7/1978 | Hernandez |
| 4,736,002 A | 4/1988 | Allen |
| 4,847,340 A | 7/1989 | Allen |
| 4,859,757 A | 8/1989 | Pellon |
| 4,967,299 A | 6/1990 | Ewen |
| 5,143,968 A | 9/1992 | Diehl |
| 5,149,741 A | 9/1992 | Alper et al. |
| 5,185,398 A | 2/1993 | Kehr |
| 5,218,071 A | 6/1993 | Tsutsui |
| 5,387,208 A | 2/1995 | Ashton |
| 5,475,075 A | 12/1995 | Brant |
| 5,539,056 A | 7/1996 | Yang |
| 5,669,894 A | 9/1997 | Goldman |
| 5,714,554 A | 2/1998 | Sustic |
| 5,723,546 A | 3/1998 | Sustic |
| 6,232,391 B1 | 5/2001 | Sambasivam et al. |
| 7,199,180 B1 | 4/2007 | Simmons et al. |
| 7,262,251 B2 * | 8/2007 | Kanderski ............ C09J 123/142 525/240 |
| 9,334,431 B2 | 5/2016 | Hamann et al. |
| 2002/0019507 A1 | 2/2002 | Karandinos |
| 2003/0096896 A1 | 5/2003 | Wang |
| 2005/0054779 A1 | 3/2005 | Zhou |
| 2006/0184146 A1 | 8/2006 | Suzuki |
| 2007/0135563 A1 | 6/2007 | Simmons et al. |
| 2009/0270825 A1 | 10/2009 | Wciorka |
| 2010/0029851 A9 | 2/2010 | Jiang |
| 2010/0305531 A1 | 12/2010 | Bach et al. |
| 2011/0021102 A1 | 1/2011 | Inoue et al. |
| 2011/0021103 A1 | 1/2011 | Alpher |
| 2012/0328805 A1 | 12/2012 | Davis |
| 2013/0225752 A1 | 8/2013 | Tse |
| 2014/0134910 A1 | 5/2014 | Mansfield |
| 2014/0199545 A1 | 7/2014 | Moriguchi |
| 2014/0358100 A1 | 12/2014 | Remmers et al. |
| 2014/0371703 A1 | 12/2014 | Davis et al. |
| 2016/0121014 A1 | 5/2016 | Remmers |

FOREIGN PATENT DOCUMENTS

| | | |
|---|---|---|
| WO | WO2011/022523 | 2/2011 |
| WO | WO2012/129489 | 9/2012 |
| WO | WO2013/039261 | 3/2013 |
| WO | WO2013/039263 | 3/2013 |
| WO | WO2014/034916 | 3/2014 |

* cited by examiner

ELASTIC ATTACHMENT HOT MELT ADHESIVE COMPOSITION AND A DISPOSABLE ABSORBENT ARTICLE MADE WITH THE SAME

CROSS-REFERENCE TO RELATED APPLICATION

This application claims the benefit of the U.S. Provisional Application having the Ser. No. 62/370,433.

BACKGROUND

In the area of industrial adhesives, hot melt adhesives are commonly used to bond together a wide variety of articles including disposable absorbent articles comprising nonwoven substrates e.g. adult incontinence products, disposable diapers, sanitary napkins, bed pads, puppy pads, medical dressings, etc.

There can be multiple hot melt adhesives used in the manufacture of a disposable absorbent article. For example, in the manufacture of a disposable diaper, adhesives are used in construction (e.g. bonding the back sheet to the nonwoven and optionally the absorbent pad), elastic attachment (e.g. bonding the elastic material to the back sheet in for example the leg or waist area) and for the core stabilization (e.g. applying an adhesive to the absorbent core to increase the strength of the core).

Hot melt adhesives for elastic attachment applications formulated with polyolefin polymers tend to have higher creep, especially at body temperatures and under stress, than those formulated with styrene block copolymers (SBC). It would be desirable to use polyolefin polymers in hot melt adhesives for elastic attachment applications as they tend to have a lower odor.

There is a need in the industry for an olefin based hot melt adhesive that can be used for elastic attachment and that provides acceptable creep when exposed to body temperatures under stress.

SUMMARY

In one aspect, the invention features a hot melt adhesive composition including from about 3 to about 10% by weight of a first propylene-based copolymer having a melt index measured by ASTM D1238 (190° C., 2.16 kg) of no greater than about 5, a second propylene-based polymer with a viscosity at 190° C. of no greater than about 5000 cps, a first tackifying agent having a softening point of at least about 90° C. and from about 5% by weight to about 20% by weight of a plasticizer.

In one embodiment, the first tackifying agent is present at from about 20% to about 70% by weight. In another embodiment, the first tackifying agent has a softening point of at least about 110° C. In still another embodiment, the first propylene-based copolymer has an ethylene content of no less than about 10. In a different embodiment, the first propylene-based copolymer is present at from about 3 to about 7% by weight.

In one embodiment, the second propylene-based polymer has a viscosity at 190° C. of no greater than about 3,000 cps, or even no greater than about 2,000 cps. In another embodiment, the second propylene-based polymer is present at from about 7% to about 20% by weight. In still another embodiment, the hot melt adhesive composition further comprises a third polymer.

In one embodiment, the first propylene-based copolymer, second propylene-based polymer, third polymer, first tackifying agent and plasticizer makes up at least 90% of the adhesive composition. In another embodiment, the total of the first propylene based copolymer and the second propylene based polymer is no less than about 10% by weight.

In one embodiment, the hot melt adhesive composition has a viscosity of from about 3,000 cps to about 20,000 cps at 177° C. In a different embodiment, the hot melt adhesive has a creep (37.8° C., 4 hours) of no greater than 35%.

In another aspect, the invention features a disposable absorbent article including a first substrate and an elastic material; and an adhesive composition including from about 3 to about 10% by weight of a first propylene-based copolymer having a melt index by ASTM D1238 (190° C., 2.16 kg) of no greater than about 5, a second propylene based polymer with a viscosity at 190° C. of no greater than about 5000 cps, a tackifying agent with a melt point of at least 90° C. and from about 5% by weight to about 20% by weight of a plasticizer wherein the adhesive composition is in contact with the elastic material and the first substrate.

In one embodiment, the disposable absorbent article is selected from the group including an adult incontinence product and a diaper. In a different embodiment, the disposable absorbent article is a diaper. In another embodiment, the disposable absorbent article is an adult incontinence product. In still another embodiment, the adhesive composition bonds the elastic material to the first substrate resulting in creep resistant gathers.

The fast rate of set, high tensile strength and low creep make it possible to use the inventive hot melt adhesive composition for elastic attachment in the manufacture of a disposable absorbent article.

Hot Melt Adhesive Composition

The invention features a hot melt adhesive composition based on olefin polymers that can be used for elastic attachment in the manufacture of a disposable article. The hot melt adhesive includes from about 3 to about 10% by weight of a first propylene-based polymer having a melt index measured by ASTM D1238 (190° C., 2.16 kg) of no greater than about 5, a second propylene based polymer with a viscosity at 190° C. of no greater than about 5000 cps, a first tackifying agent having a softening point of at least about 90° C. and from about 5% by weight to about 20% by weight of a plasticizer.

The first propylene-based polymer, second propylene-based polymer, third polymer, first tackifying agent and plasticizer can make up at least 80%, at least 85% by weight, at least 90% by weight, or even at least 95% by weight of the composition.

The first propylene-based polymer, second propylene-based polymer, third polymer, first tackifying agent, second tackifying agent and plasticizer can make up at least 80%, at least 85% by weight, at least 90% by weight, or even at least 95% by weight of the composition.

The hot melt adhesive composition has a viscosity of from about 3,000 to about 30,000 cps, from about 3,000 to about 20,000 cps, or even from about 5,000 to about 15,000 cps when measured at a temperature of 177° C.

The hot melt adhesive composition can have a creep (37.8° C., 4 hours) of no greater than about 35%, no greater than about 30%, or even no greater than about 25%.

Polymer

The adhesive composition includes at least two different propylene-based polymers. A propylene-based polymer is defined as a polymer comprising at least 50% by weight of propylene. Useful propylene-based polymers for the first and/or second polymer include propylene homopolymers. Alternatively, one or both of the two different propylene-based polymers can be copolymers of propylene with one or more other monomers (e.g. ethylene, butene, pentene, octene, etc.). The propylene-based polymers can be based entirely on olefins, i.e. do not contain any functional groups. The propylene-based polymers can comprise greater than 75% by weight propylene or even greater than 80% by weight propylene. The propylene-based polymers can have a polydispersity (Mw/Mn) of less than about 5, less than about 3, from about 1 to about 4, or even about 2. Useful propylene-based polymers can have a density of no greater than about 0.90, no greater than about 0.89, no greater than about 0.88, or even from about 0.86 to about 0.88. Useful propylene-based polymers include single-site (e.g. metallocene) catalyzed propylene-based polymers.

The first polymer is a propylene-based polymer. The first polymer can be a propylene-based copolymer. The first propylene-based polymer has a melt index as measured by ASTM D1238 (190° C., 2.16 kg) of no greater than 7, no greater than 5, from about 1 to about 7, or even from about 2 to about 5.

The first propylene-based polymer has an Mw (obtained using High Temperature GPC Molecular Weight Distribution Analysis test method found in the EXAMPLES section) of greater than about 250000 grams/mole, greater than about 275000 grams/mole, or even from about 250000 to about 350000 grams/mole.

The first propylene-based polymer can have a comonomer content of no less than about 10 weight %, no less than about 12% by weight, or even from about 10% by weight to about 20% by weight. In one embodiment, the comonomer is ethylene.

The first propylene-based polymer can be present in the composition at no greater than about 10%, no greater than about 8% by weight, between about 3% by weight and about 10% by weight, or even between about 3% by weight and about 7% by weight. Useful commercially available first propylene-based polymers include VISTAMAXX 6102 from ExxonMobil Chemical (Houston, Tex.).

The second polymer is a propylene-based polymer. The second propylene-based polymer has a viscosity at 190° C. of no greater than about 5000 cps, no greater than about 3000 cps, no greater than about 2000 cps, or even from about 750 to about 3000 cps. The second propylene based polymer can have an Mw (obtained using High Temperature GPC Molecular Weight Distribution Analysis test method found in the EXAMPLES section) of less than about 60000 grams/mole, less than about 50000 grams/mole, or even from about 20,000 grams/mole to about 60,000 grams/mole.

The second propylene-based polymer can have a comonomer content of no greater than about 12% by weight, no greater than about 10% by weight, from about 5% to about 15% by weight, or even from about 0% to about 12% by weight.

The second propylene-based polymer can be present in the adhesive composition at no less than about 7% by weight, no less than about 10% by weight, from about 7% to about 20% by weight, or even from about 10% to about 18% by weight. Useful commercially available second propylene-based polymers include LICOCENE PP6102 and LICOCENE PP2602 from Clariant International Ltd. (Muttenz, Switzerland) and VISTAMAXX 8880 from ExxonMobil Chemical (Houston, Tex.).

The total of the first propylene-based polymer and the second propylene-based polymer can be no less than about 10% by weight, from about 10% by weight to about 30% by weight, or even from about 12% by weight to about 25% by weight.

The hot melt adhesive can also include a third polymer. The third polymer can be an olefin. The third polymer can be selected from the group consisting of ethylene-based and propylene-based polymers. The third polymer can have a melt index as measured by ASTM D1238 (190° C., 2.16 kg) of greater than 7, between about 8 and about 50, or even between about 8 and 20. The third polymer can be used to build strength into the adhesive while not impacting the viscosity as much as the first polymer. When the third polymer is present, it can be present at from about 5% by weight to about 25% by weight, from about 7% to about 20% by weight, or even from about 7% by weight to about 15% by weight.

Useful commercially available first propylene-based polymers includes VISTAMAXX 6202 from ExxonMobil Chemical (Houston, Tex.).

Tackifying Agent

The hot melt adhesive includes a first tackifying agent and optionally a second tackifying agent.

The first and second tackifying agents can be at least partially hydrogenated. Suitable classes of first and second tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof; low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

The first tackifying agent is solid at room temperature. The first tackifying agent has a softening point of at least about 90° C., at least about 100° C., at least about 110° C., at least about 115° C., at least about 125° C., or even from about 110° C. to about 150° C. Useful first tackifying agents are commercially available under a variety of trade designations including, e.g., the ESCOREZ series of trade designations from Exxon Mobil Chemical Company (Houston, Tex.) including ESCOREZ 5600 and 5415 and the EASTOTAC series of trade designations from Eastman Chemical (Kingsport, Tenn.) including EASTOTAC H-130 and RESINALL R1030 from Akrochem Corporation (Akron, Ohio).

The adhesive composition can include from about 20% by weight to about 70% by weight, from about 30% by weight to about 67% by weight, or even from about 45% by weight to about 65% by weight of the first tackifying agent.

The second tackifying agent can have a softening point less than that of the first tackifying agent.

Plasticizer

The hot melt adhesive composition includes a plasticizer. Suitable plasticizers include, e.g., naphthenic oils, paraffinic oils (e.g., cycloparaffin oils), mineral oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil), derivatives of oils, glycerol esters of fatty acids, polyesters, polyethers, lactic acid derivatives, solid plasticizers (e.g. benzoates) and combinations thereof. In one embodiment, the plasticizer is an oil.

Useful commercially available plasticizers include CALSOL 5550 oil from Calumet Specialty Products Partners, LP (Indianapolis, Ind.), KAYDOL OIL from Sonneborn (Tarrytown N.Y.) PARAPOL polybutene from Exxon Mobil Chemical Company (Houston, Tex.), OPPANOL polyisobutylene from BASF (Ludwigshafen, Germany), KRYSTOL 550 mineral oil from Petrochem Carless Limited (Surrey, England), PURETOL 15 mineral oil from Petro Canada Lubricants Inc. (Mississauga, Ontario) and BENZOFLEX 352 a room temperature solid benzoate plasticizer from Eastman Chemical Company (Kingsport, Tenn.).

The plasticizer is present at no greater than 20% by weight, no greater than 18% by weight, from about 5% by weight to about 20% by weight, or even from about 10% to about 18% by weight.

Additional Components

The adhesive composition optionally includes additional components including, e.g., stabilizers, antioxidants, additional polymers (e.g. styrenic block copolymers, amorphous poly-alpha olefins, polyethylene copolymers), additional tackifying agents, waxes, adhesion promoters, ultraviolet light stabilizers, colorants (e.g., pigments and dyes), fillers, surfactants, co-extrusion coatings, packaging films, wetness indicators, superabsorbents and combinations thereof.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J., and ETHYL 702 4,4'-methylene bis(2,6-di-tert-butylphenol). When present, the adhesive composition preferably includes from about 0.1% by weight to about 2% by weight antioxidant.

Disposable Absorbent Article

The adhesive composition can be applied to (i.e. such that it is in direct contact with) or incorporated in a variety of substrates including, e.g., films (e.g., polyolefin (e.g., polyethylene and polypropylene) films), release liners, porous substrates, cellulose substrates, sheets (e.g., paper, and fiber sheets), paper products, woven and nonwoven webs, fibers (e.g., synthetic polymer fibers and cellulose fibers) and tape backings.

The adhesive composition is also useful in a variety of applications and constructions including, e.g., disposable absorbent articles including, e.g., disposable diapers, adult incontinence products, sanitary napkins, medical dressings (e.g., wound care products) bandages, surgical pads, pet training pads (e.g. puppy pads) and meat-packing products and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue) and elastics.

The adhesive composition is useful on substrates made from a variety of fibers including, e.g., natural cellulose fibers such as wood pulp, cotton, silk and wool; synthetic fibers such as nylon, rayon, polyesters, acrylics, polypropylenes, polyethylene, polyvinyl chloride, polyurethane, and glass; recycled fibers, and various combinations thereof.

Various application techniques can be used to apply the composition to a substrate including, e.g., slot coating, spraying including, e.g., spiral spraying and random spraying, screen printing, foaming, engraved roller, extrusion and melt blown application techniques.

Methods of Making a Disposable Absorbent Article

The hot melt adhesive composition is used for elastic attachment applications, which include bonding elastic material (e.g. strands, film, etc.) to a component of the disposable absorbent article. The elastic material can be coated with the hot melt adhesive composition while in a stretched form and then bonded to a film (e.g. polyethylene, polypropylene, etc.) or a nonwoven substrate. The elastic material coated with the hot melt adhesive can also be bonded between two such substrates. This process results in creep resistant gathers once the tension is removed.

The adhesive can alternatively be applied to the film or nonwoven substrate and then the elastic material bonded to it.

The hot melt adhesive can be used as an elastic attachment adhesive in forming the ear/tab of the disposable absorbent article.

Alternatively, the hot melt adhesive can further be used as an elastic attachment adhesive to help elasticize either the leg holes or the waist of the disposable absorbent article.

The invention will now be described by way of the following examples. All parts, ratios, percents and amounts stated in the Examples are by weight unless otherwise specified.

EXAMPLES

Test Procedures

Test procedures used in the examples and throughout the specification, unless stated otherwise, include the following. The amounts of raw materials listed in Tables 2 and 3 are in weight percent.

High Temperature GPC Molecular Weight Distribution Analysis

The GPC molecular weight distribution curve of each polymer in Table 1 was obtained using a high temperature HPLC system with BHT-stabilized 1,2,4-Trichlorobenzene (TCB) mobile phase. The molecular weight data, was calculated versus polystyrene standards.

GPC System: Agilent PL-GPC 220
Mobile Phase: TCB stabilized with 0.0125% BHT
Temperature: 160C
Columns: PLgel 10 um mixed-B (3)
Flow rate: 1.0 ml/min
Injection Volume: 200 uL
Concentration: 6.0 mg/ml (0.009 g/1.5 mL)

Viscosity Test Method

Viscosity is determined in accordance with ASTM D-3236 entitled, "Standard Test Method for Apparent viscosity of Adhesives and Coating Materials," (Oct. 31, 1988), using a Brookfield Thermosel viscometer Model RVDV 2 and a number 27 spindle. The results are reported in centipoise (cps).

Creep Determination

Bond Preparation

The hot melt adhesive is applied in molten form to 3 LYCRA 800 dtex strands (pre-stretched to 300%) using a Nordson SURE WRAP nozzle, an application temperature of 177° C. and a coat weight of 47.3 mg/strand/meter (1.2 mg/strand/inch). The adhesive was coated on the pre-stretched elastic strands, the strands were then laminated between a nonwoven (UNIPRO 45 available from Midwest Filtration LLC) and a polyethylene back sheet (DH284 available from Clopay).

Bond Testing

1. Staple one end of the multi-strand elastic attachment lamination to the edge of a sturdy piece of cardboard with the nonwoven facing up.
2. Extend the sample to 100% of full extension being careful not to overextend the back sheet.
3. Mark the sample where it reaches the 300 mm marking on the cardboard.
4. Relax the sample until the sample marking reaches the 285 mm marking on the cardboard, and staple the other end of the attachment. The sample is now secured at 95% of full extension.
5. After at least five samples have been attached in this same manner, cut through the individual strands of elastic at each end of the attachments, allowing the strands to be able to move within the lamination. Be careful not to cut the entire polyethylene sheet.
6. Condition the board with the anchored test specimens at 37.8° C. (100° F.) for four hours.
7. Remove the board and specimens from the oven and mark the polyethylene where the elastic is still bonded, represented by the gathered portion of the attachment.
8. Measure the length of the initial bond (285 mm) and the bond length at four where the elastic is still bonded; calculate percent creep per calculation below.
9. Report average of five samples Calculations $$\text{Percent Creep} = \frac{\text{initial length} - \text{length at } X \text{ hours}}{\text{initial length}} \times 100$$

TABLE 1

Polymer Properties

| | First polymer VISTAMAXX 6102 | Second polymer VISTAMAXX 8880 | Third polymer VISTAMAXX 6202 |
|---|---|---|---|
| Supplier | Exxon Mobil Chem. Co. | Exxon Mobil Chem. Co. | Exxon Mobil Chem. Co. |
| Polymer Type | PP/PE Copolymer | PP/PE Copolymer | PP/PE Copolymer |
| Ethylene content (weight %) | 16 | 6 | 15 |
| Melt Index ASTM D1238 (190° C./2.16 kgs) | 3 | Not Available | 9.1 |
| Viscosity @ 190° C. (cP) | Not Available | 1200 | Not Available |
| Molecular Weight (Mw) by GPC (grams/mole) | 315000 | 42200 | 215000 |
| Density | .862 | .879 | .861 |

TABLE 2

| | Examples | | | | |
|---|---|---|---|---|---|
| | Comp 1* | Control 1 | Example 1 | Example 2 | Example 3 |
| VISTAMAXX 6102 | | 2 | 3 | 5 | 5 |
| VISTAMAXX 8880 | | 14 | 13 | 16.9 | 12.5 |
| VISTAMAXX 6202 | | 14 | 13 | 9.1 | 12.5 |
| EASTOTAC H130 | | 60 | 59 | 54.5 | 55 |
| CALSOL 550 | | 10 | 12 | 14.5 | 15 |
| Molten Viscosity at 177° C. (cP) | 10625 | 10200 | 8500 | 13100 |
| Creep - 37.8° C. (100° F.), 4 hour (%) | 25 | 44 | 31 | 24 | 20 |

*Comparative 1 is NW1002P ZP a styrene block copolymer (SBC) based adhesive commercially available from HB Fuller Company

TABLE 3

| | Examples | | | |
|---|---|---|---|---|
| | Example 4 | Example 5 | Example 6 | Example 7 |
| VISTAMAXX 6102 | 5 | 5 | 5 | 5 |
| VISTAMAXX 8880 | 10 | 16 | 16.9 | 12.1 |
| VISTAMAXX 6202 | 10 | 15 | 9.1 | 12.3 |
| EASTOTAC H130 | | 52 | 54.5 | |
| ESCOREZ 5415 | 55 | | | |
| ESCOREZ 5600 | | | | 53 |
| CALSOL 550 | | 12 | 14.5 | 15 |
| BENZOFLEX 352 | 20 | | | |
| Additives | | | | 2.6 |
| Molten Viscosity at 177° C. (cP) | 7575 | 19400 | 8500 | 10450 |
| Creep - 37.8° C. (100° F.), 4 hour (%) | 22 | 28 | 24 | 31 |

The adhesive compositions were prepared by combining and mixing the components in the percentages set forth in Table 2 in a sigma blade mixer operating at 177° C.

The amount in the additives row, includes the total amount of antioxidant, co-extrusion coating and packaging film present in the adhesive.

Other embodiments are within the claims.

What is claimed is:

1. A hot melt adhesive composition comprising:
   a. from about 3 to about 10% by weight of a first propylene-based copolymer that is single-site catalyzed having a melt index measured by ASTM D1238 (190° C., 2.16 kg) of no greater than about 5,
   b. a second propylene-based polymer that is single-site catalyzed with a viscosity at 190° C. of no greater than about 5000 cps,
   c. a first tackifying agent having a softening point of at least about 90° C. and
   d. from about 5% by weight to about 20% by weight of a plasticizer.
2. The hot melt adhesive composition of claim 1 wherein the first tackifying agent is present at from about 20% to about 70% by weight.
3. The hot melt adhesive composition of claim 1 wherein the first tackifying agent has a softening point of at least about 110° C.
4. The hot melt adhesive composition of claim 1 wherein the first propylene-based copolymer has an ethylene content of no less than about 10.

5. The hot melt adhesive composition of claim 1 wherein the first propylene-based copolymer is present at from about 3% by weight to about 7% by weight.

6. The hot melt adhesive composition of claim 1 wherein the second propylene-based polymer has a viscosity at 190° C. of no greater than about 3,000 cps.

7. The hot melt adhesive composition of claim 1 wherein the second propylene-based polymer has a viscosity at 190° C. of no greater than about 2,000 cps.

8. The hot melt adhesive composition of claim 1 wherein the second propylene-based polymer is present at from about 7% to about 20% by weight.

9. The hot melt adhesive composition of claim 1 further comprising a third polymer.

10. The hot melt adhesive composition of claim 9 wherein the first propylene-based copolymer, second propylene-based polymer, third polymer, first tackifying agent and plasticizer makes up at least 90% of the adhesive composition.

11. The hot melt adhesive composition of claim 1 wherein the total of the first propylene-based copolymer and the second propylene based polymer is no less than about 10% by weight.

12. The hot melt adhesive composition of claim 1 having a viscosity of from about 3,000 cps to about 20,000 cps at 177° C.

13. The hot melt adhesive composition of claim 1 having a creep (37.8° C., 4 hours) of no greater than 35%.

* * * * *